US012053799B2

(12) United States Patent
Matsui

(10) Patent No.: US 12,053,799 B2
(45) Date of Patent: Aug. 6, 2024

(54) POWER SUPPLY

(71) Applicant: OLYMPUS CORPORATION, Hachioji (JP)

(72) Inventor: Shunsuke Matsui, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 1420 days.

(21) Appl. No.: 16/514,143

(22) Filed: Jul. 17, 2019

(65) Prior Publication Data
US 2019/0336112 A1 Nov. 7, 2019

Related U.S. Application Data

(63) Continuation of application No. PCT/JP2017/001392, filed on Jan. 17, 2017.

(51) Int. Cl.
B06B 1/02 (2006.01)
A61B 8/00 (2006.01)
A61B 17/00 (2006.01)
A61B 17/32 (2006.01)
A61N 7/00 (2006.01)
G01N 29/34 (2006.01)

(52) U.S. Cl.
CPC .... B06B 1/0215 (2013.01); A61B 17/320068 (2013.01); B06B 1/0207 (2013.01);
(Continued)

(58) Field of Classification Search
CPC ............... B06B 1/0215; B06B 1/0207; A61B 17/320068; A61B 8/56;
(Continued)

(56) References Cited

U.S. PATENT DOCUMENTS

2008/0048598 A1  2/2008  Shibuya
2011/0273465 A1  11/2011  Konishi et al.
(Continued)

FOREIGN PATENT DOCUMENTS

JP  2014-113057 A  6/2014
JP  2016-32429 A   3/2016
(Continued)

OTHER PUBLICATIONS

Apr. 11, 2019 International Search Report issued in International Application No. PCT/JP2017/001392.
(Continued)

Primary Examiner — Arnold M Kinkead
(74) Attorney, Agent, or Firm — Oliff PLC

(57) ABSTRACT

A power supply connected to an ultrasonic treatment instrument. The power supply includes an oscillator, a field programmable gate array (FPGA), and a drive circuit. The oscillator generates a basic clock. The FPGA receives the basic clock generated by the oscillator. The FPGA generates a pulse width modulation (PWM) wave for driving a ultrasonic transducer based on the basic clock. The drive circuit is connected to the FPGA, and digitally amplifies the PWM wave to output the amplified PWM wave. The FPGA outputs the PWM wave when an output signal for driving the ultrasonic treatment instrument is input, and the PWM wave is modulated by comparing a value of first data representing a sine wave in constant current control with a value of second data representing a reference wave. The FPGA outputs a rectangular wave with a predetermined duty ratio when the output signal is not input.

10 Claims, 5 Drawing Sheets

(52) U.S. Cl.
CPC ....... *A61B 8/56* (2013.01); *A61B 2017/00137* (2013.01); *A61N 7/00* (2013.01); *G01N 29/343* (2013.01); *G01N 29/346* (2013.01); *G01N 29/348* (2013.01)

(58) Field of Classification Search
CPC .... A61B 2017/00137; A61B 17/22004; A61N 7/00; G01N 29/343; G01N 29/346; G01N 29/348
USPC .................................................. 331/61, 154
See application file for complete search history.

(56) References Cited

U.S. PATENT DOCUMENTS

| | | | |
|---|---|---|---|
| 2016/0023021 A1 | 1/2016 | Liu et al. | |
| 2016/0037079 A1 | 2/2016 | Gocho et al. | |
| 2017/0202595 A1* | 7/2017 | Shelton, IV | ....... A61B 18/1445 |

FOREIGN PATENT DOCUMENTS

| | | |
|---|---|---|
| WO | 2011/052390 A1 | 5/2011 |
| WO | 2015/015877 A1 | 2/2015 |

OTHER PUBLICATIONS

Aug. 1, 2019 English Translation of the IPRP issued in International Application No. PCT/JP2017/001392.
Apr. 11, 2017 International Search Report issued in International Application No. PCT/JP2017/001392.

* cited by examiner

| ADRR | ROM_DATA(hex) |
|---|---|
| 0 | 0 |
| 1,31 | 40 |
| 2,30 | 80 |
| 3,29 | C0 |
| 4,28 | 100 |
| 5,27 | 140 |
| 6,26 | 180 |
| 7,25 | 1C0 |
| 8,24 | 200 |
| 9,23 | 240 |
| 10,22 | 280 |
| 11,21 | 2C0 |
| 12,20 | 300 |
| 13,19 | 340 |
| 14,18 | 380 |
| 15,17 | 3C0 |
| 16 | 3FF |
F I G. 2
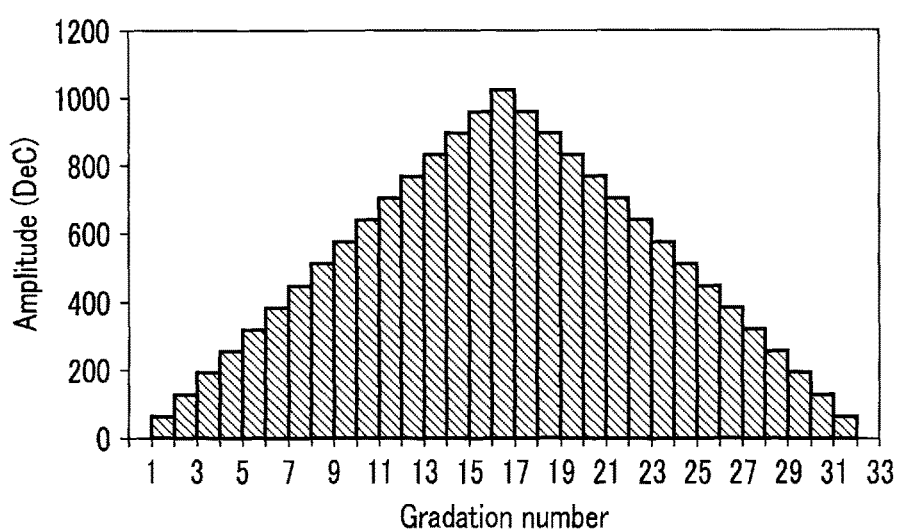
F I G. 3

POWER SUPPLY

CROSS-REFERENCE TO RELATED APPLICATIONS

This application is a Continuation Application of PCT Application No. PCT/JP2017/001392, filed Jan. 17, 2017, the entire contents of which are incorporated herein by reference.

FIELD

The embodiments relate to a power supply for an ultrasonic treatment instrument.

BACKGROUND

An ultrasonic treatment instrument is known as one of the treatment instruments for treating living tissue. The ultrasonic treatment instrument is a treatment instrument configured to treat the living tissue by bringing a tip part, which vibrates by ultrasonic vibration of an ultrasonic transducer, into contact with the living tissue.

In the ultrasonic treatment instrument, a constant current control is performed to keep a current supplied to the ultrasonic transducer constant so that amplitude of vibration at the tip part is stable even if load fluctuation of the living tissue occurs.

SUMMARY

A power supply according to an aspect is connected to an ultrasonic treatment instrument. The ultrasonic treatment instrument includes an ultrasonic transducer. The power supply includes an oscillator, a field programmable gate array (FPGA), and a drive circuit. The oscillator generates a basic clock. The FPGA receives the basic clock generated by the oscillator. The FPGA generates a pulse width modulation (PWM) wave for driving the ultrasonic transducer at a constant current based on the basic clock. The drive circuit is connected to the FPGA. The drive circuit digitally amplifies the PWM wave to output the amplified PWM wave. The FPGA outputs the PWM wave when an output signal for driving the ultrasonic treatment instrument is input. The FPGA outputs a rectangular wave with a predetermined duty ratio when the output signal is not input.

Advantages of the embodiments will be set forth in the description which follows, and in part will be obvious from the description, or may be learned. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

FIG. 2 is a diagram showing an example of a LUT for generating a reference wave.

FIG. 3 is a diagram showing a triangular wave generated by the LUT of FIG. 2.

DETAILED DESCRIPTION

Figure 1:
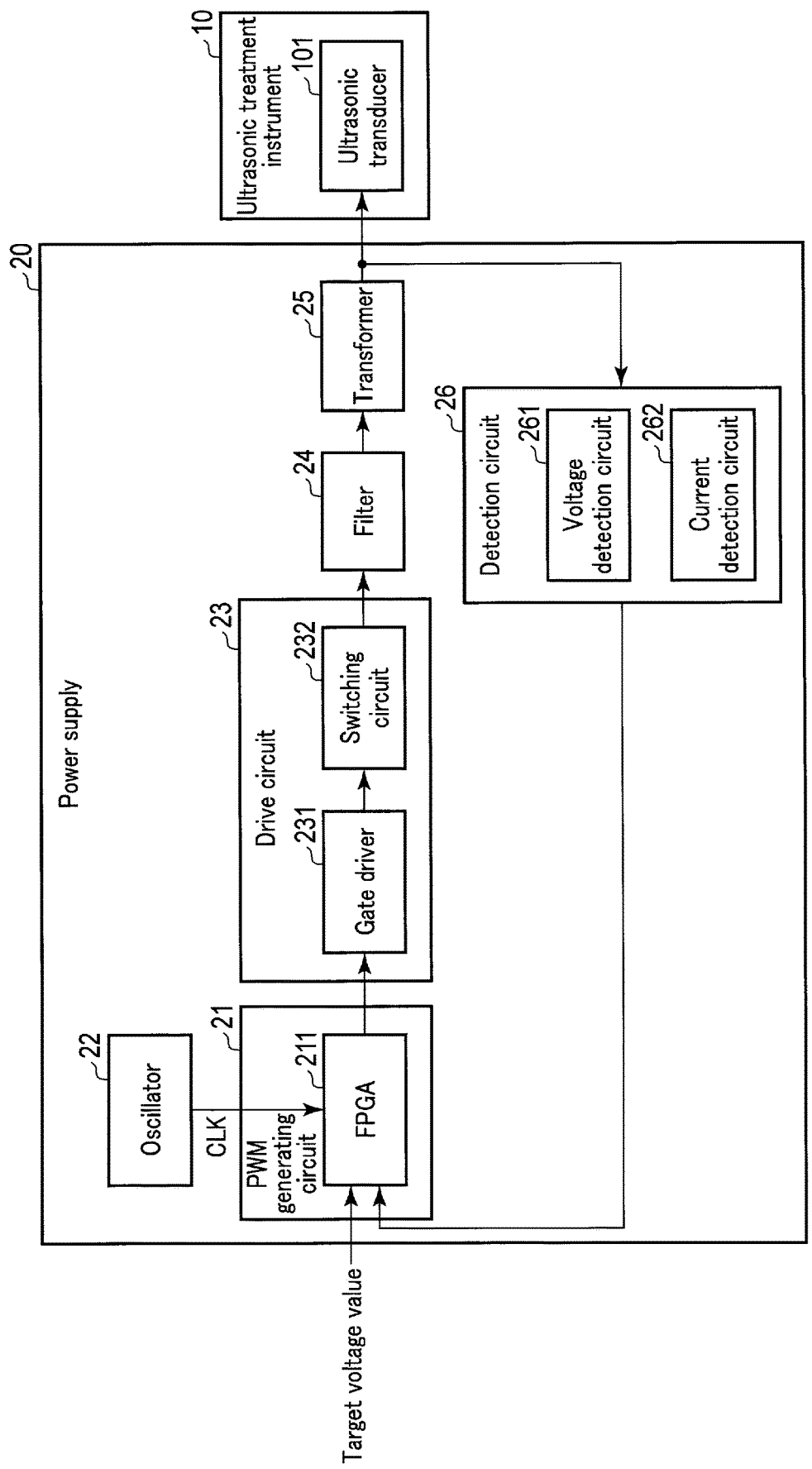
FIG. 1 is a block diagram showing a main configuration of a power supply according to an embodiment.

Hereinafter, an embodiment will be described with reference to the drawings. FIG. 1 is a block diagram showing a main configuration of a power supply according to an embodiment. A power supply 20 is electrically connected to an ultrasonic treatment instrument 10. The power supply 20 outputs an ultrasonic drive signal to an ultrasonic transducer 101 so as to ultrasonically vibrate the ultrasonic transducer 101 of the ultrasonic treatment instrument 10 at constant amplitude. The power supply 20 includes a PWM generating circuit 21, an oscillator 22, a drive circuit 23, a filter 24, a transformer 25, and a detection circuit 26.

The PWM generating circuit 21 is configured by a field programmable gate array (FPGA) 211. The FPGA 211 generates a PWM wave for generating an ultrasonic drive signal based on an output voltage applied to the ultrasonic transducer 101 detected by the detection circuit 26, an output current flowing to the ultrasonic transducer 101, and a target power value (or a current value, etc.) which is an output signal for driving the ultrasonic treatment instrument 10 for constant current control of the ultrasonic transducer 101 (in other words, an output signal related to an output of the ultrasonic treatment instrument 10). Details of the FPGA 211 will be described later.

The oscillator 22 is, for example, a crystal oscillator, and generates a basic clock CLK used by the FPGA 211. Although details will be described later, the FPGA 211 generates a reference wave for generating the PWM wave based on the basic clock CLK generated by the oscillator 22. The reference wave is, for example, a triangular wave or a sawtooth wave.

The drive circuit 23 includes a gate driver 231 and a switching circuit 232, and constitutes a digital amplifier (class D amplifier circuit) together with the PWM generating circuit 21. The gate driver 231 turns on or off a high-side FET switch and a low-side FET switch provided in the switching circuit 232 based on the signal output from the FPGA 211 of the PWM generating circuit 21. The switching circuit 232 includes an FET bridge circuit having the high-side FET switch and the low-side FET switch, and a bootstrap circuit for boosting a high side voltage to be higher than a voltage of a voltage source for driving the drive circuit 23, and outputs a signal obtained by amplifying the signal output from the FPGA 211 of the PWM generating circuit 21 in accordance with a switching operation by the gate driver 231.

The filter 24 is a restoration circuit that performs low-pass filter processing for the amplified PWM wave output from the drive circuit 23 to restore an analog signal having a frequency of the ultrasonic drive signal from the PWM wave.

The transformer 25 amplifies a voltage of the analog signal that has passed through the filter 24 according to a winding ratio, and outputs the amplified voltage to the ultrasonic transducer 101 as the ultrasonic drive signal.

The detection circuit 26 includes a voltage detection circuit 261 and a current detection circuit 262. The voltage detection circuit 261 takes in the ultrasonic drive signal output from the transformer 25, and outputs a digital voltage value of the taken-in ultrasonic drive signal to the FPGA 211 of the PWM generating circuit 21. The current detection circuit 262 takes in the ultrasonic drive signal output from the transformer 25, and outputs a digital current value of the taken-in ultrasonic drive signal to the FPGA 211 of the PWM generating circuit 21.

Next, an operation of the FPGA 211 will be described. The FPGA 211 outputs different signals to the drive circuit 23 at the time of driving the ultrasonic treatment instrument 10 (the ultrasonic transducer 101) and at the time of non-driving the ultrasonic treatment instrument 10 (the ultrasonic transducer 101). Here, the time of driving the ultrasonic treatment instrument 10 (the ultrasonic transducer 101) refers to a state in which the target power value is input to the FPGA 211. The target power value is, for example, a power value set by an operation of an operation button provided on the ultrasonic treatment instrument 10 when a user uses the ultrasonic treatment instrument 10. In addition, different target power values may be set according to operation modes of the ultrasonic treatment instrument 10, and the target power value may be set by the user selecting one of the operation modes. In addition, the time of non-driving the ultrasonic treatment instrument 10 (the ultrasonic transducer 101) refers to a state in which the target power value is not input to the FPGA 211 at power-on or the like.

First, an operation at the time of driving the ultrasonic treatment instrument 10 (the ultrasonic transducer 101) will be described. At the time of driving the ultrasonic treatment instrument 10 (the ultrasonic transducer 101), the FPGA 211 performs an operation for outputting the PWM wave to the drive circuit 23. The PWM wave is generated by (1) generation of a constant current controlled sine wave, (2) generation of a reference wave, and (3) comparison of the sine wave and the reference wave. In the following description, although it is described that the generation of the reference wave is performed after the generation of the sine wave, the generation of the sine wave and the generation of the reference wave may be sequentially performed or performed simultaneously.

In order to generate the constant current controlled sine wave, the FPGA 211 generates constant current control data and frequency control data so as to set the power value currently supplied to the ultrasonic transducer 101 calculated from the digital voltage value and digital current value acquired from the detection circuit 26 to the target power value. The constant current control data is, for example, digital data representing a direct current (DC) signal indicating a voltage value of an ultrasonic drive signal necessary for driving the ultrasonic transducer 14 at a constant current. The frequency data is, for example, digital data representing an alternating current (AC) signal indicating a frequency value of the ultrasonic drive signal.

After generating the constant current control data and the frequency control data, FPGA 211 generates data representing the constant current controlled sine wave by multiplying the constant current control data by the frequency control data.

In addition, in order to generate data representing the reference wave, the FPGA 211 generates a lookup table (LUT) for generating the reference wave according to a frequency of the clock CLK input from the oscillator 22. First, the FPGA 211 determines resolution of the reference wave. The resolution is the number of data constituting the reference wave. Resolution of the PWM wave generated in the FPGA 211 is also determined by the resolution of the reference wave. The resolution is expressed by the following (Equation 1) using a frequency of a basic clock CLK and a frequency of the reference wave.

Resolution=(Frequency of Basic Clock)/(Frequency of Reference Wave)  (Equation 1)

For example, when the frequency of the basic clock CLK is 32 MHz and the frequency of the reference wave is 1 MHz, the resolution is 32. As can be seen from Equation 1, if the frequency of the basic clock CLK changes, the resolution also changes. Therefore, the resolution can be changed by changing the frequency of the basic clock CLK by multiplying or dividing the frequency of the basic clock CLK.

FIG. 2 is a diagram showing an example of a LUT for generating a reference wave. FIG. 2 shows an example of the LUT when the reference wave is a triangular wave and the resolution is 32. In addition, since the reference wave is a periodic wave, data for one wave may be generated as the LUT.

When the resolution is 32, 32 addresses, ADRR 0 to ADRR 31 in a ROM for storing the LUT, are designated. Data for the reference wave is stored one by one in each address. For example, when a triangular wave whose amplitude is 10 bits long (1023) is generated, each address ADRR stores a value obtained by dividing 3FF (hex) (=1023 (dec)) by 16 as shown in FIG. 2. In addition, the amplitude of the triangular wave does not have to be 10 bits long and is appropriately set. When the triangular wave is generated, only the resolution may be variable and the amplitude may be fixed.

FIG. 3 is a diagram showing a triangular wave (for one wave) generated by the LUT of FIG. 2. As shown in FIG. 3, the triangular wave generated by the LUT in FIG. 2 is a triangular wave taking a value of 1023 (dec) when the gradation number is 16.

Figure 4:
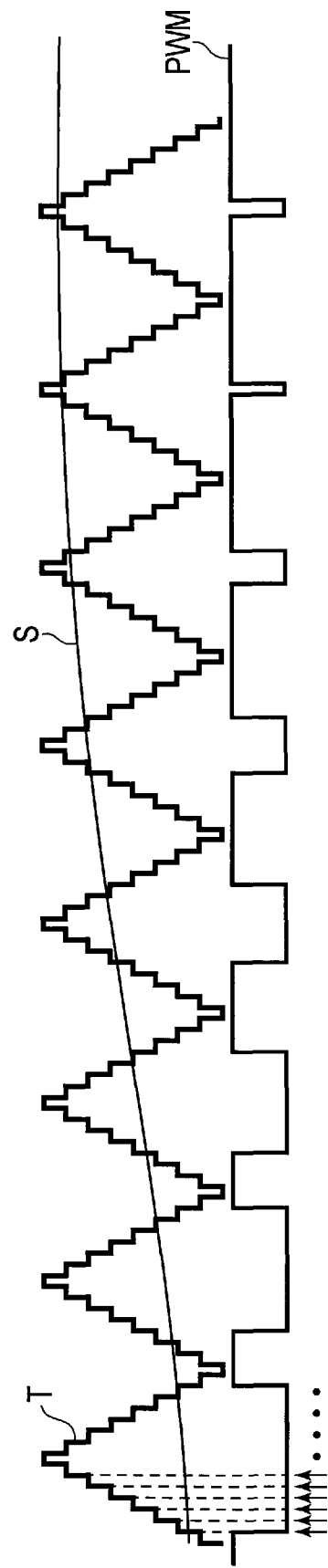
FIG. 4 is a diagram showing the concept of PWM wave generation.

After generating both the data representing the constant current controlled sine wave and the data representing the reference wave, the FPGA 211 generates the PWM wave by comparing the sine wave and the reference wave. FIG. 4 is a diagram showing the concept of PWM wave generation. As shown in FIG. 4, the FPGA 211 compares the sine wave and the reference wave with each other data by data. In addition, the PWM wave is generated according to a relationship of the following Equation 2. Here, sin_wave_unsined in Equation 2 indicates a data value (absolute value) of the sine wave S, and triangle_wave indicates a data value of the triangular wave T. In addition, pwm_out indicates a data value of the generated PWM wave PWM.

sin_wave_unsined>triangle_wave:pwm_out=1 sin_wave_unsined<triangle_wave:pwm_out=0  (Equation 2)

For example, the PWM wave generated by comparison with the triangular wave generated based on the LUT of FIG. 2 becomes a PWM wave with a frequency of 1 MHz and 32 gradations. In this way, the resolution of the PWM wave is determined by the resolution of the reference wave. Basically, it is possible to restore the sine wave with high accuracy in the filter 24 by increasing the resolution of the PWM wave. However, if the resolution of the PWM wave is made too high, an attenuation amount at the time of transmission of the PWM wave becomes large. When the PWM wave is attenuated, restoration property of the sine wave in the filter 24 is degraded. Therefore, it is desirable to increase the resolution of the PWM wave, that is, the resolution of the reference wave, to such an extent that no significant attenuation occurs. As described above, such adjustment of the resolution of the reference wave can be performed by changing the frequency of the basic clock CLK.

In addition, as described above, the PWM wave generated by the FPGA 211 is input to the drive circuit 23 constituting a digital amplifier together with the PWM generating circuit 21. The PWM wave amplified in the drive circuit 23 is converted to an analog signal in the filter 24, then amplified again in the transformer 25, and applied to the ultrasonic transducer 101. Thus, the ultrasonic transducer 101 is driven at a constant current.

Figure 5:
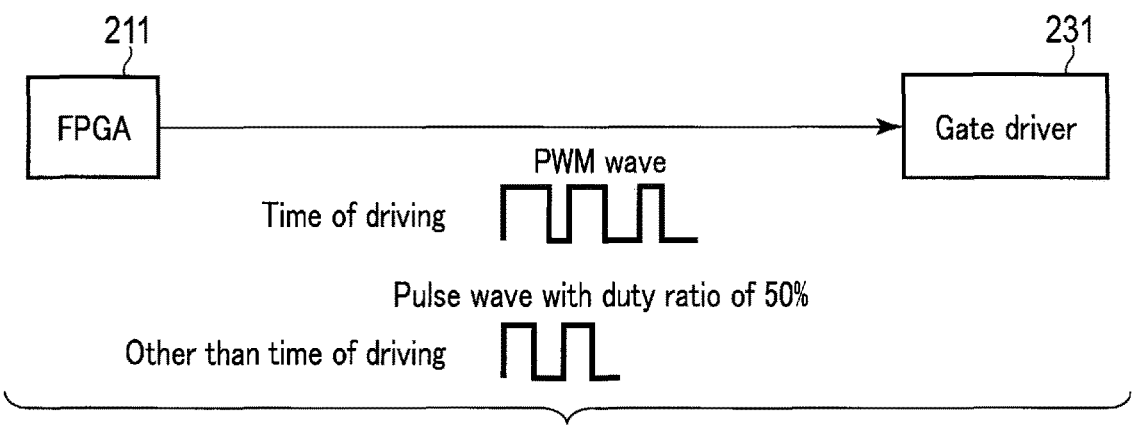
FIG. 5 is a diagram showing an output signal of an FPGA in comparison at the time of driving an ultrasonic transducer and at the time of non-driving the ultrasonic transducer.

Next, an operation at the time of non-driving the ultrasonic treatment instrument 10 (the ultrasonic transducer 101) will be described. FIG. 5 is a diagram showing an output signal of the FPGA 211 in comparison at the time of driving the ultrasonic transducer and at the time of non-driving the ultrasonic transducer. As described above, at the time of driving the ultrasonic treatment instrument 10 (the ultrasonic transducer 101), the FPGA 211 outputs the PWM wave to the gate driver 231 of the drive circuit 23 as shown in FIG. 5. Meanwhile, at the time of non-driving the ultrasonic treatment instrument 10 (the ultrasonic transducer 101) at power-on of the power supply 20, the FPGA 211 outputs a rectangular wave with a duty ratio of 50% to the gate driver 231 of the drive circuit 23 as shown in FIG. 5.

Figure 6:
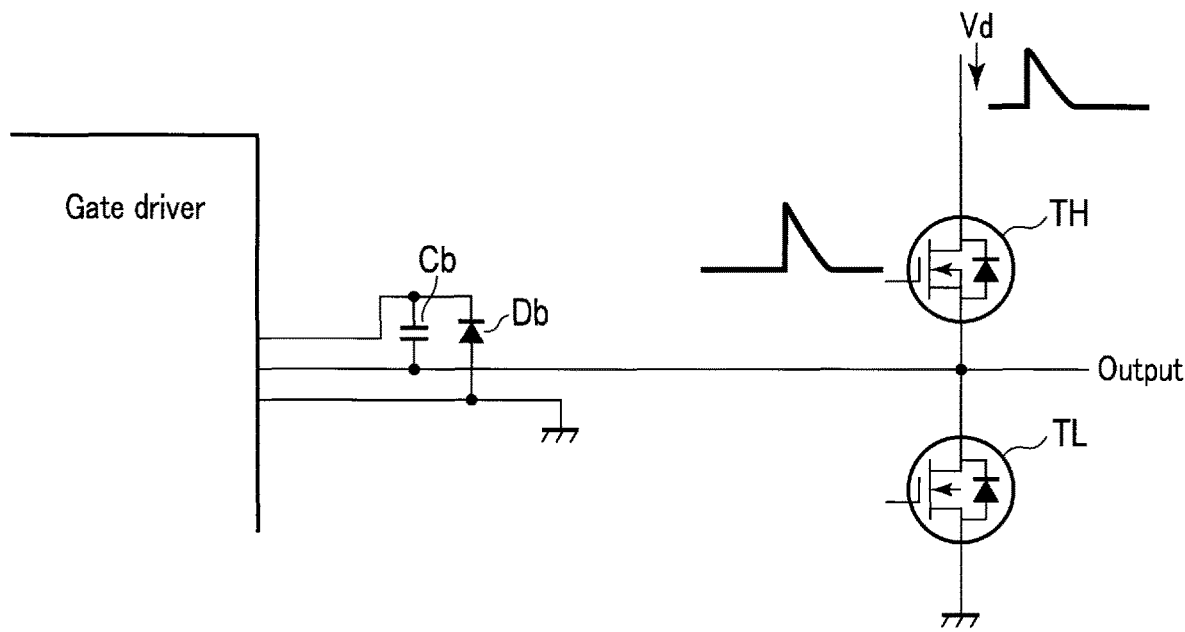
FIG. 6 is a diagram showing an internal state of a drive circuit at power-on of the power supply when a rectangular wave with a duty ratio of 50% is not output from the FPGA to the drive circuit.

FIG. 6 is a diagram showing an internal state of a drive circuit 23 at power-on of the power supply 20 (at the time of non-driving the ultrasonic treatment instrument 10) when a rectangular wave with a duty ratio of 50% is not output from the FPGA 211 to the drive circuit 23. The drive circuit 23 in FIG. 6 shows only the minimum configuration.

As described above, the drive circuit 23 includes the gate driver 231 and the switching circuit 232. The switching circuit 232 mainly includes an FET bridge circuit in which a high-side FET switch TH and a low-side FET switch TL are coupled to each other, and a bootstrap circuit. The FET switch TH and the FET switch TL are both n-type MOSFETs. In addition, a drain of the FET switch TH is connected to a voltage source of the drive circuit 23. In addition, a source of the FET switch TH and a drain of the FET switch TL are connected to each other, and an output terminal of the drive circuit 23 is provided at a contact therebetween. Further, a source of the FET switch TL is grounded. In addition, gates of the FET switch TH and the FET switch TL are connected to the gate driver 231. That is, the FET switch TH and the FET switch TL are turned on or off by application of a gate voltage from the gate driver 231. In addition, the gate driver 231 is connected to the bootstrap circuit including a bootstrap diode Db and a bootstrap capacitor Cb. Due to a boosting operation of the bootstrap circuit by the switching operation of the FET switch TH and the FET switch TL, the gate voltage of the FET switch TH is further boosted with respect to the voltage of the voltage source. The PWM wave is amplified by the boosting operation of the gate voltage of the high-side FET switch TH.

In such a configuration, when the FPGA 211 does not output the rectangular wave with the duty ratio of 50% to the drive circuit 23 at the power-on of the power supply 20, a DC voltage is input from the FPGA 211 to the gate driver 231. This is because the target power value is not input to the FPGA 211 at the power-on of the power supply 20, and the FPGA 211 does not generate the constant current controlled sine wave. In response to the input of the DC voltage, the gate driver 231 turns on the FET switch TH and the FET switch TL, but at this time a large current is generated in an output line of the FET. This is because the FET switch TH and the FET switch TL are in a turned-on state and the bootstrap capacitor Cb which has been charged once by turning on the FET switch TH and the FET switch TL is thus completely discharged. Due to the generation of such a large current, large noise occurs at the output terminal or there is a risk of damaging the FET switches.

Figure 7:
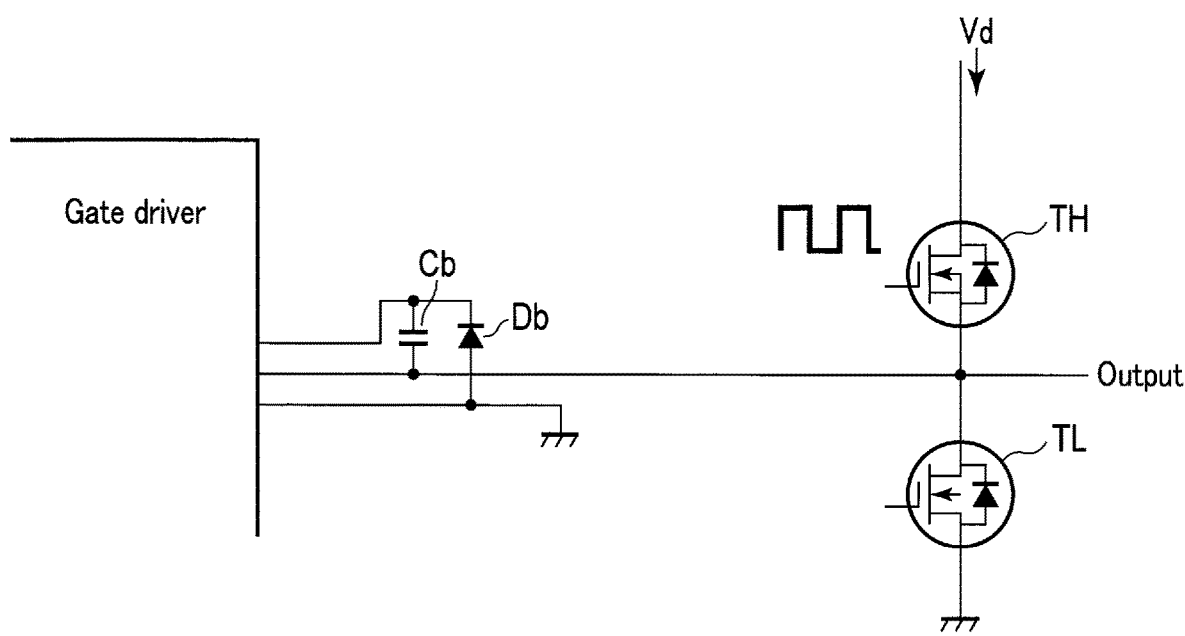
FIG. 7 is a diagram showing an internal state of a drive circuit at power-on of the power supply when a rectangular wave with a duty ratio of 50% is output from the FPGA to the drive circuit.

FIG. 7 is a diagram showing an internal state of the drive circuit 23 at power-on of the power supply 20 (at the time of non-driving the ultrasonic treatment instrument 10) when the rectangular wave with the duty ratio of 50% is output from the FPGA 211 to the drive circuit 23.

When the rectangular wave with the duty ratio of 50% is output from the FPGA 211 to the drive circuit 23 at the power-on of the power supply 20, the gate driver 231 switches the FET switch TH and the FET switch TL. Therefore, charge and discharge of the bootstrap capacitor Cb are repeated, and a large current is not generated in the output line of the FET switch. As a result, a large noise does not occur at the output terminal, and there is no risk of damaging the FET switch.

As described above, according to the present embodiment, since the generation of the constant current controlled sine wave to the generation of the PWM wave is performed in the FPGA, a circuit scale of the power supply can be reduced.

Meanwhile, in the configuration in which the generation of the PWM wave is performed in the FPGA, the DC voltage is output from the FPGA to the drive circuit when the PWM wave is not generated at power-on or the like. On the other hand, in the present embodiment, the rectangular wave with the duty ratio of 50% is output from the FPGA to the drive circuit at the power-on or the like. As a result, the generation of a large current due to the output of the DC voltage to the drive circuit can be suppressed.

Here, in the present embodiment, the rectangular wave with the duty ratio of 50% is output from the FPGA to the drive circuit. The duty ratio may not necessarily be 50%. However, in consideration of a charge and discharge balance of the bootstrap capacitor, it is desirable that the duty ratio is 50%.

In addition, in the present embodiment, the time of driving and the time of non-driving the ultrasonic treatment instrument 10 (the ultrasonic transducer 101) are determined based on the presence or absence of the input of the target power value to the FPGA 211. On the other hand, the control circuit other than the FPGA 211 determines the time of driving and the time of non-driving the ultrasonic treatment instrument 10 (the ultrasonic transducer 101), and a configuration may be employed in which the FPGA 211 is controlled based on the result of the determination.

Additional advantages and modifications will readily occur to those skilled in the art. Therefore, the embodiment in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A power supply connected to an ultrasonic treatment instrument including an ultrasonic transducer, the power supply comprising:
   an oscillator configured to generate a basic clock;
   a field programmable gate array (FPGA) configured to receive the basic clock generated by the oscillator and generate a pulse width modulation (PWM) wave configured to drive the ultrasonic transducer at a constant current based on the basic clock, the FPGA being configured to:
      when an target power value configured to drive the ultrasonic treatment instrument is input, output the PWM wave, the PWM wave being modulated by comparing a value of first data representing a sine wave in constant current control with a value of second data representing a reference wave, the first data being generated based on the target power value, the second data being a triangular wave generated based on a predetermined amplitude and a resolution determined according to a frequency of the basic clock, and
      when the target power value is not input, output a rectangular wave with a predetermined duty ratio; and
   a drive circuit configured to be connected to the FPGA and digitally amplify the PWM wave to output an amplified PWM wave.

2. The power supply according to claim 1, wherein the predetermined duty ratio is 50%.

3. The power supply according to claim 1, wherein the drive circuit includes a gate driver and a field-effect transistor (FET) bridge circuit.

4. The power supply according to claim 1, wherein the FPGA is configured to generate a lookup table storing the second data representing the reference wave based on the frequency of the basic clock.

5. The power supply according to claim 1, further comprising a restoration circuit configured to restore an ultrasonic drive signal for driving the ultrasonic transducer at the constant current from the PWM wave output from the drive circuit, and output the ultrasonic drive signal to the ultrasonic transducer.

6. An operation method of a power supply, the operation method comprising:
   determining, by a supply device connected to an ultrasonic treatment instrument, whether a target power value configured to drive the ultrasonic treatment instrument including an ultrasonic transducer is input;
   in response to determining that the target power value is not input, outputting a rectangular wave with a predetermined duty ratio;
   in response to determining that the target power value is input, generating, by an oscillator, a basic clock;
   generating, by a field programmable gate array (FPGA), first data representing a sine wave in constant current control and second data representing a reference wave, the first data being generated based on the target power value, the second data being a triangular wave generated based on a predetermined amplitude and a resolution determined according to a frequency of the basic clock;
   generating and modulating, by the FPGA, a pulse width modulation (PWM) wave by comparing a value of the first data with a value of the second data;
   digitally amplifying the PWM wave by a drive circuit connected to the FPGA; and
   outputting, by the drive circuit, the amplified PWM wave.

7. The operation method of the power supply according to claim 6, wherein the predetermined duty ratio is 50%.

8. The operation method of the power supply according to claim 6, wherein the drive circuit includes a gate driver and a field-effect transistor (FET) bridge circuit.

9. The operation method of the power supply according to claim 6, further comprising generating, by the FPGA, a lookup table storing the second data based on the frequency of the basic clock.

10. The operation method of the power supply according to claim 6, further comprising:
    restoring, by a restoration circuit, an ultrasonic wave drive signal from the PWM wave output from the drive circuit, the ultrasonic wave drive signal being configured to drive the ultrasonic transducer, and
    outputting, by the restoration circuit, the ultrasonic drive signal to the ultrasonic transducer.

* * * * *